US 11,335,443 B1

(12) United States Patent
Pinskiy et al.

(10) Patent No.: US 11,335,443 B1
(45) Date of Patent: May 17, 2022

(54) PHENOTYPIC PATIENT DATA DERIVATION FROM ECONOMIC DATA

(71) Applicant: OpenNano Pte. Ltd., Franklin Lakes, NJ (US)

(72) Inventors: Vadim Pinskiy, Fair Lawn, NJ (US); Ashwin Gopinath, Palo Alto, CA (US); Kim E. Drexler, Oxford (GB); TJ Brunette, Seattle, WA (US); George Markou, Foster City, CA (US); Serge Faguet, Moscow (RU); Petr Boiko, Moscow (RU); Yuliya Seregina, Singapore (SG)

(73) Assignee: OpenNano Pte. Ltd., Franklin Lake, NJ (US)

( * ) Notice: Subject to any disclaimer, the term of this patent is extended or adjusted under 35 U.S.C. 154(b) by 0 days.

(21) Appl. No.: 17/013,782

(22) Filed: Sep. 7, 2020

(51) Int. Cl.
| | | |
|---|---|---|
| *G16H 10/60* | (2018.01) | |
| *G16B 20/00* | (2019.01) | |
| *G06K 9/62* | (2022.01) | |
| *G06N 20/00* | (2019.01) | |
| *G16B 40/00* | (2019.01) | |
| *G06N 3/08* | (2006.01) | |

(52) U.S. Cl.
CPC ........... *G16H 10/60* (2018.01); *G06K 9/6268* (2013.01); *G06N 20/00* (2019.01); *G16B 20/00* (2019.02); *G16B 40/00* (2019.02); *G06N 3/08* (2013.01)

(58) Field of Classification Search
CPC .......... G16H 10/60; G06N 20/00; G06N 3/08; G16B 40/00; G16B 20/00; G06K 9/6268
See application file for complete search history.

(56) References Cited

U.S. PATENT DOCUMENTS

| 7,941,329 | B2 | 5/2011 | Kenedy et al. |
|---|---|---|---|
| 8,015,028 | B2 | 9/2011 | Summer et al. |
| 8,321,372 | B1 | 11/2012 | Rakshit et al. |
| 8,818,932 | B2 | 8/2014 | Nolan et al. |
| 10,140,422 | B2 | 11/2018 | Rust et al. |
| 10,169,852 | B1 | 1/2019 | Putman et al. |
| 10,481,579 | B1 | 11/2019 | Putman et al. |
| 10,578,850 | B1 | 3/2020 | Putman et al. |
| 2008/0251070 | A1 | 10/2008 | Pinskiy et al. |
| 2014/0108045 | A1 | 4/2014 | Afshar et al. |
| 2014/0297324 | A1 | 10/2014 | Duftler et al. |
| 2015/0294420 | A1 | 10/2015 | Hu |
| 2016/0117469 | A1 | 4/2016 | Tesanovic et al. |
| 2016/0171177 | A1 | 6/2016 | Caffarel et al. |
| 2016/0171383 | A1 | 6/2016 | Narain et al. |

(Continued)

FOREIGN PATENT DOCUMENTS

| WO | 2019195095 A1 | 10/2019 |
|---|---|---|
| WO | 2019212848 A1 | 11/2019 |
| WO | 2020113237 A1 | 6/2020 |

*Primary Examiner* — Michael Tomaszewski
*Assistant Examiner* — Jay M. Patel
(74) *Attorney, Agent, or Firm* — Schonauer Law LLC; Matthew J. Schonauer

(57) ABSTRACT

The application of deep machine learning controllers to derive models of phenotypic patient data from primary economic data is disclosed herein. The use of systems and methods of employing the model are disclosed and useful in predicting treatment outcomes and compound efficacy, suggesting treatment plans and compounds, and clinical studies and phenotypical correlation studies in conjunction with medical records, economic data sets or combinations thereof.

14 Claims, 4 Drawing Sheets

(56) References Cited

U.S. PATENT DOCUMENTS

| | | |
|---|---|---|
| 2017/0262604 A1 | 9/2017 | Francois |
| 2018/0082030 A1* | 3/2018 | Allen .................... G16H 70/20 |
| 2018/0182475 A1* | 6/2018 | Cossler ................. G16H 50/50 |
| 2019/0228126 A1 | 7/2019 | Oh |
| 2019/0237171 A1 | 8/2019 | Kain et al. |
| 2020/0005900 A1* | 1/2020 | Cha ....................... G16H 50/30 |
| 2020/0013155 A1 | 1/2020 | Putman et al. |
| 2020/0051679 A1* | 2/2020 | Bostic ................... G16H 50/30 |
| 2020/0135337 A1* | 4/2020 | Athey .................... G16B 40/00 |
| 2020/0272856 A1* | 8/2020 | Garner .................. G06Q 20/42 |
| 2020/0273373 A1* | 8/2020 | Grant .................... B33Y 50/00 |

* cited by examiner

PHENOTYPIC PATIENT DATA DERIVATION FROM ECONOMIC DATA

CROSS-REFERENCE TO RELATED APPLICATIONS

This application is a provisional patent application and makes no priority claim.

TECHNICAL FIELD

Exemplary embodiments of the present invention relate generally to the creation and use of prediction, categorization and evaluation models using artificial intelligence deep learning controllers, statistical models or numerical methods, and more specifically to systems and methods in which economic data sets or other digital databases containing traces of medically related behavior are used to model phenotypic patient data.

BACKGROUND OF THE INVENTION

Medical data are historically difficult to obtain and use in large-scale analytical settings due to a variety of factors such as regulatory issues, formatting issues (e.g., records in paper format or images) and the incompleteness of data sets, for example. Data are also limited to those obtaining medical observation. It many cases, diagnostic data are difficult to obtain, but are most often directly used to inform treatment recommendations through the application of compounds (i.e., over the counter "OTC" or prescribed medicines), biomedical devices, nutritional adjustments, lifestyle changes and the like. Diagnostic data might include, for instance, physician observations in the examination of a patient, interpretation of medical imaging tests, and diagnostic assays.

The move toward the digitization of medical data has improved the outlook for big data in the healthcare industry. However, the use of medical data is often heavily regulated, and the price of normalizing said data from their variety of sources remains high. Much of the most useful and large-scale data exist behind barriers and are not available for practical analysis. These impediments continue to depress the potential advantage that big data analytics techniques can offer. One of the problems that continues to hold back the industry is an extreme difficulty to obtain up to date and current data sets—in part due to the fractured and regulated nature of the medical data sources. Consumers—i.e., the general public—lack access to critical medical feedback without physician review that in turn often requires long lead times to schedule and complete. Therefore, while big data techniques are often employed to offer general insights into treatment pathways, there still exists a need in the art for models that can be applied to specific individuals on a current and up to date basis and can affect services based on indirect (e.g., non-medical or economic) data that have been correlated to clinical analyses.

Despite these challenges, however, it is common in the healthcare industry to pursue medical data set analyses because of the value inherent in new discoveries in biomechanics, treatment efficacies and alternatives, and diagnostic avenues. That is because—due to the complexity and variability of human biology and large existing knowledge base of diagnostic and treatment techniques, compounds, and biological mechanisms—there remains much to be discovered in ways to improve healthcare outcomes and the delivery of medical services. It is considered particularly useful to gain insights into treatment pathways that will increase the positive outcomes for patients, thereby increasing the overall health of the population and decreasing the costs associated with negative treatment outcomes.

While a great many projects have been undertaken in the art to improve treatment pathways and glean new relational links using medical data, it has also been a focus to improve data collection throughout extended treatment timelines, wherein patients are treated in a variety of settings, such as inpatient, outpatient and selfcare settings. However, these solutions are tailored to collect additional clinical data during individual treatments and do not provide a solution for deriving medically relevant models based on non-medical data. Neither are these endeavors applicable to the vast majority of individuals that are not under constant medical observation.

It is therefore an unmet need in the prior art for systems and methods for obtaining relevant, current and up to date modeled medical information for an individual derived from non-medical sources and that can be used for diagnostics and prediction of additional treatment compounds or pathways for health improvement. No known references, taken alone or in combination, are seen as teaching or suggesting the presently claimed invention.

Such a system can offer integrated prediction and analysis services during online purchase and search for OTC medication, generic medications, or be useful as a real-time analysis and predictor of additional OTC, generics, or nutritional additive products.

The data model, once trained, can be applied on any discrete individual (given that required data priors are available) to interpret analytical medical data.

The data model, once trained, can also be applied to additional applications for risk modeling, nutrition and outcome prediction and otherwise be used to achieve protein level diagnostics from non-diagnostic data.

BRIEF SUMMARY OF THE INVENTION

Exemplary embodiments of the present disclosure pertain to the use of an economic data set related to a user to create and interpret phenotypical representations of that individual. In some embodiments, an economic data set is derived from one or more databases and may comprise, for instance, historical records of orders, searches, returns, purchases or a combination thereof. In some embodiments, the data can be sourced from retail, digital services or manually provided and in some cases may comprise finalized, partially executed or abandoned order data.

An object of the present invention is to provide for the creation of a phenotype characterization (data or model) for individuals that can be used in a complementary manner with or as a replacement for traditional medical records, demographic consumption models or other models of medically related outcomes for certain analyses and to be applied on non-medical observed populations.

Another object of the present invention is to use existing economic data histories with the presented model to provide a prediction of the correlated phenotype for an individual.

In certain embodiments, the invented systems and methods are used to train a model of phenotypical patient data that may be applied to predict treatment outcomes, suggest treatment plans, and compare treatment alternatives. In some embodiments, the model is employed to further model clinical studies and phenotypical correlation studies, along with medical records, or as a substitute for medical data.

In some aspects, the disclosed technology relates to a method for deriving medically relevant information from economic data. The method includes steps for: receiving a set of training data from at least one training data source, wherein the set of training data includes one or more primary data sets having economic data, training a deep learning controller with the set of training data, wherein the deep learning controller identifies and models correlations based on the set of training data, classifying at least one relevant correlation, wherein the at least one relevant correlation corresponds to at least one economic parameter, and creating a phenotypic categorization model, wherein the phenotypic categorization model includes at least one phenotypic category derived from each of the at least one economic parameter.

In some embodiments, the set of training data received from the at least one training data source includes one or more primary data sets having economic data, and one or more secondary data sets having one or more of: demographic data, biological mechanistic data, product attribute data, clinical trial data, and medical record data. In some embodiments, the one or more primary data sets includes economic data having one or more of: retail order history data, search history data, and browsing history data.

In some aspects, the disclosed technology relates to a method for deriving medically relevant information from economic data. The method includes steps for: receiving a set of training data from at least one training data source, wherein the set of training data includes one or more primary data sets having economic data including one or more of retail order history data, search history data, and browsing history data, and one or more secondary data sets having one or more of demographic data, biological mechanistic data, product attribute data, clinical trial data and medical record data, training a deep learning controller with the set of training data, wherein the deep learning controller identifies and models correlations based on the set of training data, classifying at least one relevant correlation, wherein the at least one relevant correlation corresponds to at least one economic parameter, and creating a phenotypic categorization model, wherein the phenotypic categorization model includes at least one phenotypic category derived from each of the at least one economic parameter.

In some embodiments, the method can further include steps for: receiving a set of real data from at least one real data source, wherein the set of real data includes economic data attributable to an individual, identifying a first economic parameter from the set of real data, applying the set of real data to the phenotypic categorization model, wherein the first economic parameter is used to categorize the individual into a first phenotypic category, and deriving a first inference for the individual resulting from the first phenotypic category.

In some embodiments, the first inference may include an outcome associated with the use of a compound by the individual, a suggested treatment plan for the individual, a compound, a compound quantity, a compound application frequency or an alternative compound recommendation. In some embodiments, the first inference comprises a set of product recommendations and the method can further include the step of displaying the set of product recommendations to the individual during a search event.

In another aspect, the disclosed technology relates to a non-transitory computer-readable media comprising instructions stored thereon which, when executed by one or more processors, are configured to cause the processors to execute instructions for deriving medically relevant information from economic data, including steps for: receiving a set of training data from at least one training data source, wherein the set of training data includes one or more primary data sets having economic data including one or more of retail order history data, search history data, and browsing history data, and one or more secondary data sets having one or more of demographic data, biological mechanistic data, product attribute data, clinical trial data and medical record data, training a deep learning controller with the set of training data, wherein the deep learning controller identifies and models correlations based on the set of training data, classifying at least one relevant correlation, wherein the at least one relevant correlation corresponds to at least one economic parameter, and creating a phenotypic categorization model, wherein the phenotypic categorization model includes at least one phenotypic category derived from each of the at least one economic parameter.

It is an object of this invention to provide systems for and methods of derivation of phenotypical patient data from economic data sets of the type generally described herein, being adapted for the purposes set forth herein, and overcoming disadvantages found in the prior art. These and other advantages are provided by the invention described and shown in more detail below.

BRIEF DESCRIPTION OF THE SEVERAL VIEWS OF THE DRAWINGS

Novel features and advantages of the present invention, in addition to those mentioned above, will become apparent to those skilled in the art from a reading of the following detailed description in conjunction with the accompanying drawings wherein identical reference characters refer to identical parts and in which.

DETAILED DESCRIPTION OF THE INVENTION

Figure 1:
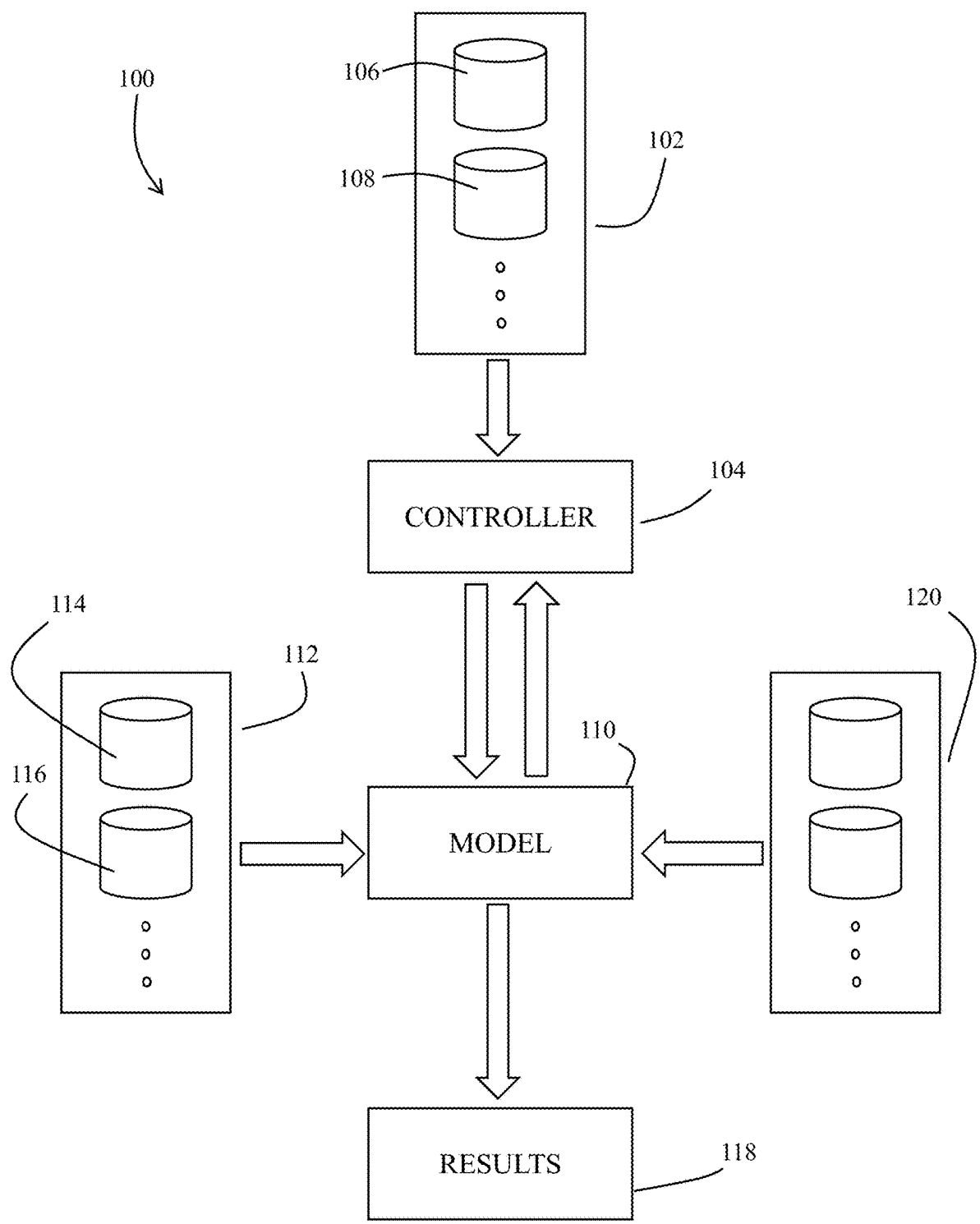
FIG. 1 is a schematic view of an exemplary embodiment of the general data structure of the related medical and economic datasets.

Exemplary embodiments of the present invention are directed to systems and methods for modeling phenotypical patient data from economic data sources. In a preferred embodiment, the order history of an individual is used to identify patient phenotypes for use in several second order outputs. Economic data sets generally have been found that are readily accessible and represent actual diagnostic data as first order approximations. This method of modeling phenotypical patient data is advantageous particularly because of the numerous difficulties inherent in obtaining and working with diagnostic, medical history and other clinical data.

As used herein when referring to input data sets related to the invented system and methods, the terms "non-medical" and "economic" are used to generally describe the use of data that are not "health information" as set forth in the HIPAA Privacy Rule 42 CFR § 160.103, namely, information that "[r]elates to the past, present, or future physical or mental health or condition of an individual; the provision of health care to an individual; or the past, present, or future payment for the provision of health care to an individual."

Machine learning/artificial intelligence (AI) models may be used to determine and model relationships between non-medical or economic data and phenotypic categorizations of individuals, thereby deriving medically relevant information. By way of example, machine learning models can be trained using multiple sources of training data, including, but not limited to: order history, browsing history, search history, banking, clinical, demographic, biomechanistic, and the like. Additionally, deployed AI models can be trained or initialized based at least in part on inputs provided from experts, such that institutional knowledge can be represented in the idealized models used to predict outcomes and suggest treatment pathways, alternatives or complements as derived from the phenotypic categorizations.

As understood by those of skill in the art, AI based classification techniques can vary depending on the desired implementation, without departing from the disclosed technology. For example, AI classification schemes can utilize one or more of the following, alone or in combination: hidden Markov models; recurrent neural networks (RNNs); convolutional neural networks (CNNs); deep learning; Bayesian symbolic methods; general adversarial networks (GANs); support vector machines; image registration methods; or applicable rule-based system. Where regression algorithms are used, they may include but are not limited to a Stochastic Gradient Descent Regressor, a Passive Aggressive Regressor, or other such algorithms.

Machine learning classification models can also be based on clustering algorithms (e.g., a mini-batch K-means clustering algorithm), a recommendation algorithm (e.g., a miniwise hashing algorithm or Euclidean locality-sensitive hashing (LSH) algorithm), or an anomaly detection algorithm, such as a local outlier factor. Additionally, machine learning models can employ a dimensionality reduction approach, such as, one or more of: a mini-batch dictionary learning algorithm, an incremental principal component analysis (PCA) algorithm, a latent Dirichlet allocation algorithm, a mini-batch K-means algorithm, or other such comparable means.

In some implementations, multiple different types of AI training models may be deployed. By way of example, general forms of machine learning can be used in order to dynamically adjust phenotypic categorizations and second- and third-order correlations related thereto, such as compound efficacies, interactions and mechanisms, and treatment efficacies, interactions and mechanisms. As recognized by those of skill in the art, the selected AI model or models do not simply contain categorization instructions but is a way to provide feedback on and improve phenotypic categorizations and prediction/suggestion operations on changing patient populations and changing compound and treatment standards. In some embodiments, the different AI models discussed herein can be deployed in a specific order to achieve dynamic feedback and iterative model improvements through repeat cycles and model tuning to optimize the phenotypic categorization of individuals based on economic data, and to further optimize useful correlative results stemming from those categorizations. First, CNNs can be used in the phenotypic categorization process to classify relevant correlations in economic data, such as order patterns, compound combinations and usage patterns, and the like. Second, reinforced learning (RL) and RL agents can be used and rewarded for achieving desired outcomes, both from the CNN classifications and for predefined desirable outcomes, such as known clinical and biomechanical pathways. The RL agents can be supervised or unsupervised. Third, GANs can be used to choose between conflicting RL agents. GANs can involve minimal human supervision, relying on humans only for selecting which RL agents to input as nodes to the GANs. Fourth, RNNs can take the winning RLs as input nodes to create a feedback and feed-forward system, so that learning can be continuous and unsupervised.

Turning to FIG. 1, a schematic diagram is shown illustrating an exemplary embodiment of the training and use of a patient phenotype modeling system and method 100. Training data sources 102 are provided to a deep learning controller at 104 for analysis to build a correlation to medical records or additional assays. At least one primary training data source 106 is provided comprising economic data such as historical purchase, search, browsing, order, return records, or combinations thereof. This data can be sourced from one or more distinct databases and from one or more vendors.

In an embodiment, for example, a primary data set that includes order history data is obtained from a training data source such as an online retailer and can be thought of as filtered data of all compounds ordered by one or more individuals over a period of time. This data can be formed into a mathematical model that reflects the effectiveness of the compounds, taking into account quantities and frequencies of orders, for instance. This data can also show which compounds are not effective for the individual as evidenced by isolated, discrete orders, for example. The data provided can be simple (e.g., linear array of single symptom orders) or complex (order history for many compounds over a lengthy time scale). In this manner, the deep learning controller classifies relevant correlations that correspond to one or more economic parameters. For example, frequency and quantity of a compound may correlate to a particular phenotypic category. In some embodiments, an analysis of order histories can provide patterns associated with given demographics, which can itself be an economic data source.

Other secondary and tertiary data sources 108 may be used as inputs during deep learning controller training 104, such as those containing demographic data, known medical and biological mechanistic data, and the like. In some embodiments, the secondary and tertiary data sources 108 will contain additional product attributes. In these cases, information for a given compound may include, for instance, the composition and chemical information (where applicable), and mechanisms and routes of operations for said compound. Other secondary and tertiary data sources 108 may optionally contain, for example, secondary data sets containing demographic information, or known clinical trial information (such as databases of clinical data provided by the U.S. National Library of Medicine). In some embodiments, natural language processing (NLP) layers can be used to interpret medical records and contextualize them into a standard form that is considered useful for a given application of the invented systems and methods. In other embodiments, the optional medical record data are sourced in a standard form. NLP layers can also be implemented to transform incoming economic data if it is desired to standardize the form of said data. Together, the training data sources 102 are used to train a deep learning controller at 104.

The deep learning controller could be embodied as, for instance, a convolutional neural network (CNN), reinforcement learning model (RL), or another numeral method model. The deep learning controller is trained at 104 to build a model 110 that correlates the primary data sources to medical records, additional or alternative assay recommendations, and phenotypical sorting generally. With the initial correlations formed for the training group, additional prediction and group classifications can be made for future inference groups. This allows that for a given economic data set for an individual, the model can predict and approximate the medical data for the patient and be used for future suggestion of additional compounds and compounds that are likely to be beneficial for the individual.

In some embodiments, a CNN is provided to train the deep learning controller 104. The CNN can contain as many layers as desired or required and may include hidden layers. The CNN can be implemented with optionally variable tuning and optimization parameters. The CNN model can be trained for as many cycles as needed, such as until the confidence for a specific value set is reached. By way of example, the model can be trained to give a sufficient prediction based on input A until a 90% confidence is reached.

Additional test data 112 comprising verifiable primary economic data sources 114 paired with known clinical data 116 may be passed through the model 110 to obtain result sets 118. Once verified, the model 110 can be passed real data source sets 120 to obtain result sets 118. The model 110 can be trained until a minimum threshold of confidence is reached. In some embodiments, the model 110 is continuously trained with the addition of new data and examples.

In some embodiments, a model for the phenotype of an individual is created from an economic data set comprising an order history from one or more retail or distribution entities. Order histories may contain, for instance, OTC compounds, other intake items such as nutritional items, topical creams and compounds, prescription medications, or combinations thereof. Training of the model may, for example, correlate order history to known medical records, other data, or combinations thereof. Primary or secondary associations or relevant correlations can be identified and classified in further embodiments through the inclusion of demographical data sets for the individuals for which the economic data were provided. Demographic data may include information such as, but not limited to, age, sex, occupation, order volume, geographic location, and the like. The creation of a phenotypic categorization model generally is realized by identifying phenotypic categories that are correlated to one or more economic parameters, which in turn are present in or derived from the primary and secondary data sets received by the deep learning controller during training or optimization processes.

The disclosed use of the model built on economic data to approximate medical data is advantageous when applied to clinical studies and phenotypical correlation studies, along with medical records, or as a substitute for medical data.

Figure 2:
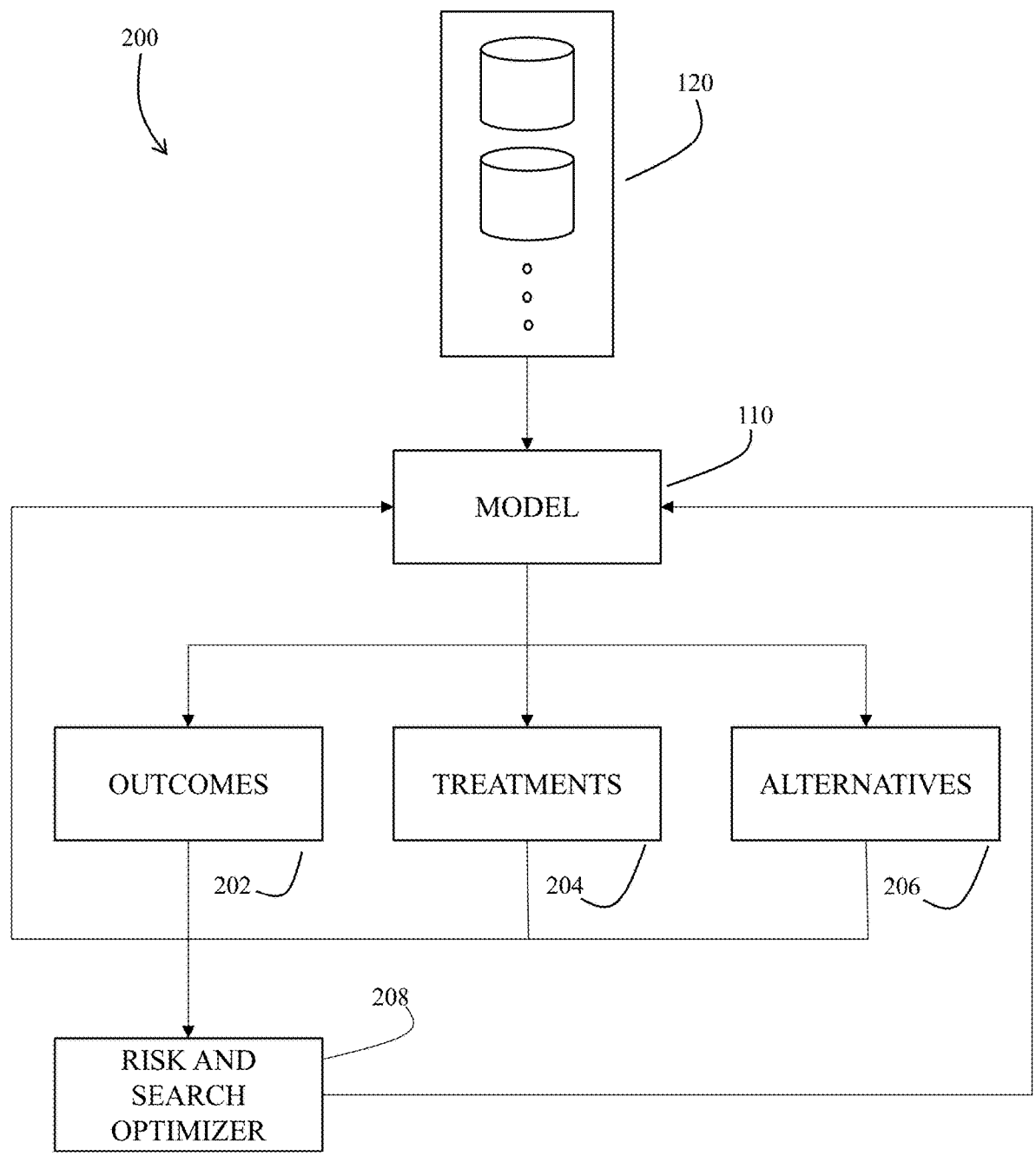
FIG. 2 is a schematic view of the integration of the invented model into outcomes, treatments and additional phenotypical use alternatives.

Turning to FIG. 2, an exemplary result set is shown once a real data source set 120 has been applied by the learned model 110, as described in connection with FIG. 1. In some embodiments, the model is used to predict the likely outcomes associated with the use of a compound for an individual, as at 202. This could include for instance, a prediction of the likelihood of success for one or more compounds that could be used to treat a particular medical condition.

In some embodiments, the model 110 is used to suggest treatment plans, as at 204. Treatment plans might include compound quantities and sequences, or frequency of intake. Some embodiments may suggest alternative compounds to those currently in use by a patient, for instance, as at 206. This may be useful as a way of suggesting generic compounds to replace prescribed compounds, particularly where individualized use history passed through the model 110 indicate a higher likelihood of success, or an acceptable cost/benefit result.

In some embodiments, the outcomes predicted by the trained model can be used to drive search-based results 208 for OTC, generics and other personalized products. This process can be based on the association of the economic data and progressive previous consumption history with the prediction enabled by the protein correlation fed into the trained model.

In some embodiments, the outcomes from the trained model can be used to drive tailored risk assessments 208 for personalized determination of risk and long-term health (and environmentally drive) outcomes. This personalized risk-score can be used independently or in combination with existing risk models. This personalized risk score can be used for health insurance, life insurance and other health related financial or pricing models for various industrial and social applications. This assessment can also be used to drive and track progression for social- or employee-driven incentive programs.

In some embodiments, the model weights of 110 can be adjusted based on the quantification of the success of 208. In some embodiments, this can take the form of total amount spent on suggested compounds or the quality of the predicted risk outcomes compared to actual. This assessment can drive the feedback to the adjustment of model inputs and the weights placed on each of the individual drivers. This feedback can improve the overall performance of the model. This feedback can be performed for individuals, groups of select demographics or select categories and/or the model as a whole.

Figure 3:
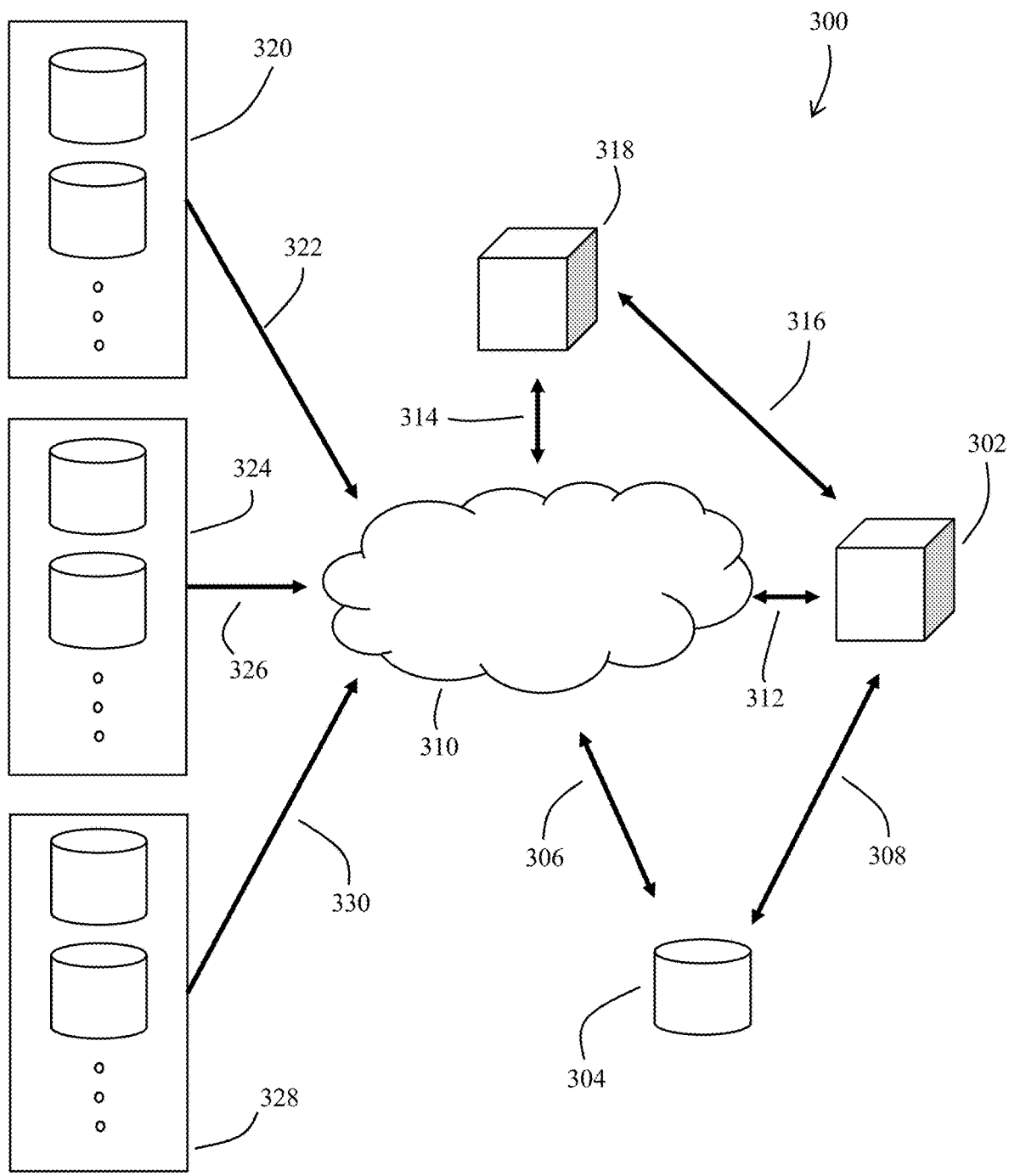
FIG. 3 is a schematic diagram of an exemplary embodiment of the invention with method of data input and the feed of data outputs on the mass of the networked system and associated integrators.

Turning to FIG. 3, a system schematic diagram is illustrated for an exemplary embodiment 300 of the disclosed invention. In this embodiment, the deep learning controller is represented at 302. Correlative models 304 may be generally stored externally via 306 or separately internally, as at 308, as the controller is trained, or stored within a controller unit itself at 302. A network is represented generally at 310 and may be an external interconnection of networks or an internal network. Implementation of the model once created is in some embodiments accomplished via an application programming interface (API) accessible via external sources via 312 and 314 or directly communicating with the controller 302 via 316. A web-facing service 318 generally can be provided for API access to the model. One or more training data sources 320 including economic data from one or more sources are accessed via 322. One or more test data sources 324 are accessed from one or more sources via 326, and one or more real data sources 328 from one or more sources are accessed via 330.

Figure 4:
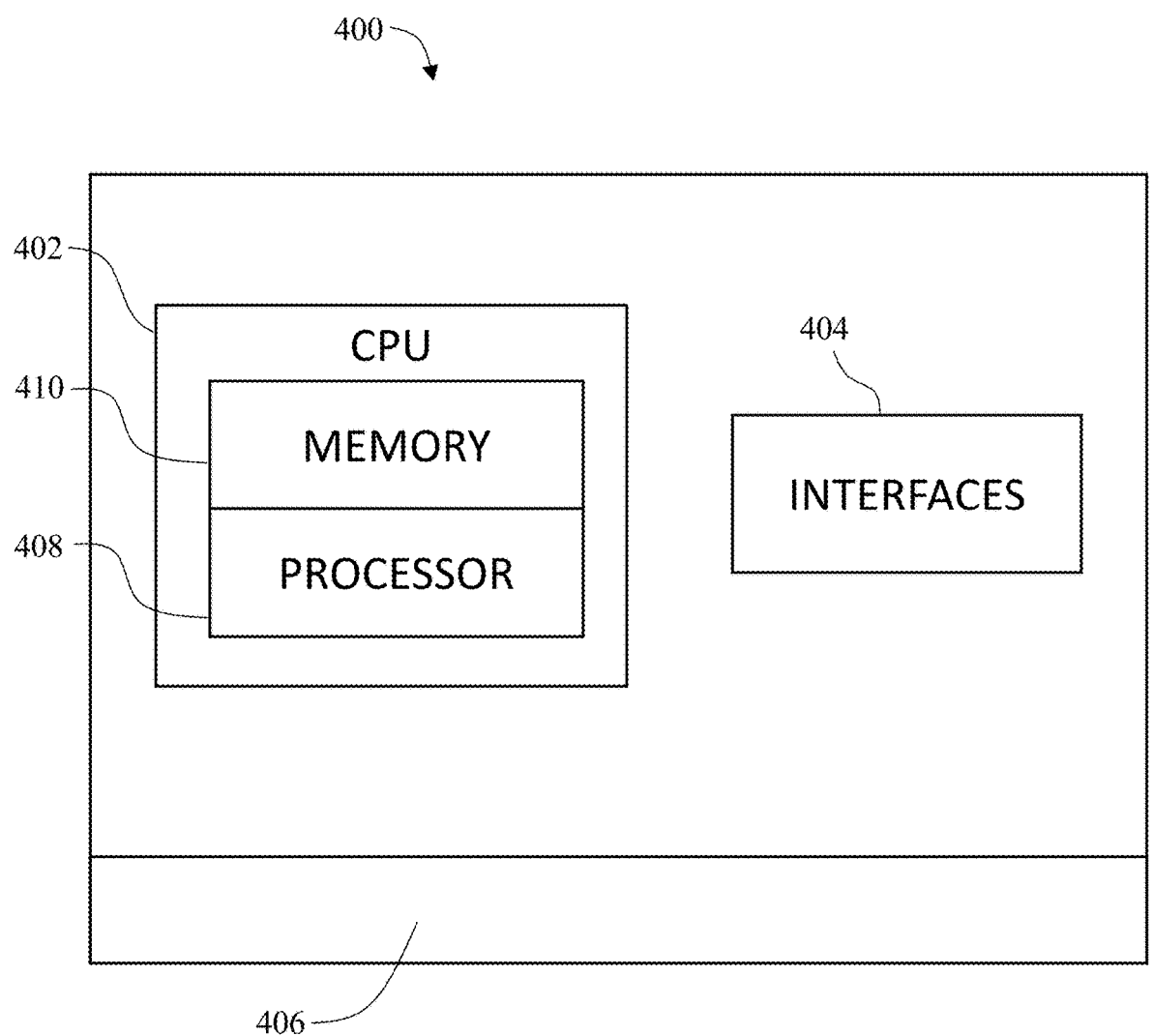
FIG. 4 illustrates an exemplary processing device that can be used to implement some aspects of the disclosed technology.

FIG. 4 illustrates an exemplary processing device that can be used to implement a system of the disclosed technology. Processing-device 400 includes a master central processing unit (CPU) 402, interfaces 404, and a bus 406 (e.g., a PCI bus). When acting under the control of appropriate software or firmware, the CPU 402 is responsible for performing various error detection monitoring and process adjustment steps of the disclosed technology. CPU 402 preferably accomplishes all these functions under the control of software including an operating system and any appropriate applications software. CPU 402 may include one or more processors 408 such as a processor from the Motorola family of microprocessors or the MIPS family of microprocessors. In an alternative embodiment, processor 408 is specially designed hardware for controlling the operations of AI or ML system 400. In a specific embodiment, a memory 410 (such as non-volatile RAM or ROM) also forms part of CPU 402. However, there are many different ways in which memory could be coupled to the system.

Interfaces 404 are typically provided as interface cards (sometimes referred to as "line cards"). Generally, they control the sending and receiving of data packets over the network and sometimes support other peripherals used with the router. Among the interfaces that can be provided are Ethernet interfaces, frame relay interfaces, cable interfaces, DSL interfaces, token ring interfaces, and the like. In addition, various very high-speed interfaces may be provided such as fast token ring interfaces, wireless interfaces, Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management. By providing separate processors for the communications-intensive tasks, these interfaces allow the master microprocessor 402 to efficiently perform routing computations, network diagnostics, security functions, etc.

Although the system shown in FIG. 4 is one specific processing device of the present invention, it is by no means the only network device architecture on which the present invention can be implemented. For example, an architecture having a single processor that handles communications as well as routing computations, etc. is often used. Further, other types of interfaces and media could also be used.

Regardless of the network device's configuration, it may employ one or more memories or memory modules (including memory 410) configured to store program instructions for the general-purpose network operations and mechanisms for roaming, route optimization and routing functions described herein. The program instructions may control the operation of an operating system or one or more applications, for example. The memory or memories may also be configured to store tables such as mobility binding, registration, and association tables, etc.

The logical operations of the various embodiments are implemented as one or more of: (1) a sequence of computer implemented steps, operations, or procedures running on a programmable circuit within a general use computer, (2) a sequence of computer implemented steps, operations, or procedures running on a specific-use programmable circuit; or (3) interconnected machine modules or program engines within the programmable circuits. The system 400 can practice all or part of the recited methods, can be a part of the recited systems, or can operate according to instructions in the recited non-transitory computer-readable storage media. Such logical operations can be implemented as modules configured to control the processor 408 to perform particular functions according to the programming of the module.

In some embodiments, the controller is trained or deployed on a standard microcontroller, a GPU based system or a cloud computing structure. Mobile computing may alternatively be deployed with sufficient optimizations for performance. Controllers can also be deployed and tuned for CPU-based processing and real time analysis.

It is understood that any specific order or hierarchy of steps in the processes disclosed is an illustration of exemplary approaches. Based upon design preferences, it is understood that the specific order or hierarchy of steps in the processes may be rearranged, or that only a portion of the illustrated steps be performed. Some of the steps may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A method for deriving medically relevant information from economic data comprising:
   receiving a set of training data from at least one training data source, wherein the set of training data comprises:
      one or more primary data sets comprising economic data from a training data source, wherein the economic data comprises retail order history data corresponding to at least one retail order history parameter and browsing history data corresponding to at least one browsing history parameter; and
      one or more secondary data sets comprising one or more of demographic data, biological mechanistic data, product attribute data, clinical trial data, and medical record data;
   training a deep learning controller with the set of training data, wherein the deep learning controller identifies and models correlations based on the set of training data;
   classifying at least one relevant correlation parameter, wherein each of the at least one relevant correlation parameter corresponds to an economic parameter comprising one of a retail order history parameter or a browsing history parameter;
   creating a phenotypic categorization model with the trained deep learning controller, wherein the phenotypic categorization model comprises at least one phenotypic category derived from each of the at least one relevant correlation parameter;
   receiving a set of real data from at least one real data source, wherein the set of real data comprises economic data attributable to an individual;
   applying the set of real data to the phenotypic categorization model, wherein a first economic parameter from the set of real data is used by the trained deep learning controller to categorize the individual into a first phenotypic category; and
   deriving a first inference for the individual resulting from the first phenotypic category.

2. The method of claim 1, wherein the first inference comprises an outcome associated with the use of a compound by the individual.

3. The method of claim 1, wherein the first inference comprises a suggested treatment plan for the individual.

4. The method of claim 3, wherein the suggested treatment plan comprises a compound, a compound quantity and a compound application frequency.

5. The method of claim 1, wherein the first inference comprises an alternative compound recommendation.

6. The method of claim 1, wherein the first inference comprises a set of product recommendations, the method further comprising the step of displaying the set of product recommendations to the individual during a search event.

7. A non-transitory computer-readable media comprising instructions stored thereon which, when executed by one or more processors, are configured to cause the processors to execute instructions for deriving medically relevant information from economic data comprising:
  receiving a set of training data from at least one training data source, wherein the set of training data comprises:
    one or more primary data sets comprising economic data from a training data source, wherein the economic data comprises retail order history data and browsing history data corresponding to at least one browsing history parameter; and
    one or more secondary data sets comprising one or more of demographic data, biological mechanistic data, product attribute data, clinical trial data, and medical record data;
  training a deep learning controller with the set of training data, wherein the deep learning controller identifies and models correlations based on the set of training data;
  classifying at least one relevant correlation parameter, wherein each of the at least one relevant correlation parameter corresponds to an economic parameter comprising one of a retail order history parameter or a browsing history parameter;
  creating a phenotypic categorization model with the trained deep learning controller, wherein the phenotypic categorization model comprises at least one phenotypic category derived from each of the at least one relevant correlation parameter;
  receiving a set of real data from at least one real data source, wherein the set of real data comprises economic data attributable to an individual;
  applying the set of real data to the phenotypic categorization model, wherein a first economic parameter from the set of real data is used by the trained deep learning controller to categorize the individual into a first phenotypic category; and
  deriving a first inference for the individual resulting from the first phenotypic category.

8. The non-transitory computer-readable media of claim 7, wherein the first inference comprises an outcome associated with the use of a compound by the individual.

9. The non-transitory computer-readable media of claim 7, wherein the first inference comprises a suggested treatment plan for the individual.

10. The non-transitory computer-readable media of claim 9, wherein the suggested treatment plan comprises a compound, a compound quantity and a compound application frequency.

11. The non-transitory computer-readable media of claim 7, wherein the first inference comprises an alternative compound recommendation.

12. The non-transitory computer-readable media of claim 7, wherein the first inference comprises a set of product recommendations, the method further comprising the step of displaying the set of product recommendations to the individual during a search event.

13. The method of claim 1, wherein the economic data of the one or more primary data sets further comprises search history data corresponding to at least one search history parameter, and wherein the economic parameter comprises one of a retail order history parameter, a browsing history parameter or a search history parameter.

14. The non-transitory computer-readable media of claim 7, wherein the economic data of the one or more primary data sets further comprises search history data corresponding to at least one search history parameter, and wherein the economic parameter comprises one of a retail order history parameter, a browsing history parameter or a search history parameter.

* * * * *